United States Patent
Rescio

(10) Patent No.: US 8,263,156 B2
(45) Date of Patent: Sep. 11, 2012

(54) FOOD SUPPLEMENT BASED ON BIOLOGICALLYCOPENE AND PROCESS TO OBTAIN BIOLOGICAL LYCOPENE

(76) Inventor: Leonardo Rescio, Corigliano d'Otranto (IT)

(*) Notice: Subject to any disclaimer, the term of this patent is extended or adjusted under 35 U.S.C. 154(b) by 726 days.

(21) Appl. No.: 12/309,905

(22) PCT Filed: Oct. 20, 2006

(86) PCT No.: PCT/IB2006/003390
§ 371 (c)(1),
(2), (4) Date: Feb. 2, 2009

(87) PCT Pub. No.: WO2008/015490
PCT Pub. Date: Feb. 7, 2008

(65) Prior Publication Data
US 2009/0304870 A1    Dec. 10, 2009

(30) Foreign Application Priority Data
Aug. 2, 2006  (IT) .............................. BA2006A0049

(51) Int. Cl.
*C11B 1/10* (2006.01)
*A23L 1/222* (2006.01)
(52) U.S. Cl. ........ 426/489; 426/615; 426/429; 426/478; 426/495
(58) Field of Classification Search .................. 426/648, 426/615, 425, 429, 478, 489, 492
See application file for complete search history.

(56) References Cited

U.S. PATENT DOCUMENTS

| | | | |
|---|---|---|---|
| 5,897,866 A * | 4/1999 | Bombardelli et al. ........ | 424/777 |
| 6,515,018 B1 * | 2/2003 | Fuhrman et al. ............. | 514/458 |
| 7,672,468 B2 * | 3/2010 | Kaiser et al. .................. | 381/314 |
| 2003/0180435 A1 * | 9/2003 | Shi ................................ | 426/615 |
| 2005/0266132 A1 * | 12/2005 | Temelli et al. ................ | 426/478 |
| 2009/0297683 A1 * | 12/2009 | Zelkha et al. ................ | 426/580 |

FOREIGN PATENT DOCUMENTS
WO    WO01/79355    * 10/2001

OTHER PUBLICATIONS

Vasapollo, G. et al. 2004. Journal of Supercritical Fluids 29:87.*
Anon. 1982. The American Heritage Dictionary, 2nd edition, Houghton Mifflin Co., Boston. p. 1061.*

* cited by examiner

*Primary Examiner* — Carolyn Paden
(74) *Attorney, Agent, or Firm* — R.Ruschena Patent Agent, LLC

(57) ABSTRACT

Innovative food supplement based on biological lycopene, which is the bulk product, i.e. the total extract, obtained by treating with supercritical carbon dioxide a suitable extraction matrix, made by 50% biological tomato berries and 50% biological dry fruits (almonds, nuts and the like) and/or other components, following a co-extractive technology. Tomato berries are conveniently de-hydrated, milled and riddled; the co-extraction matrix (dry fruits, vegetables, others) is conveniently de-hydrated and milled. The obtained total extract is directly used for preparing lycopene based food supplements, without any modification or additivation. With respect to the known commercial food supplement, based on lycopene, such biological lycopene has unique quality features: the total extract is 100% natural; absence of chemical solvents; lycopene concentration in the final natural formula (not artificial); absence dosing problems and contra-indications. In the final product, lycopene is mixed with other natural anti-oxidants, co-extracted from the used vegetables. The boxing up of the bulk product (total extract) is made in soft or hard caps in several shapes and colors or in tablets or in other way (e.g. liquid, others).

5 Claims, 1 Drawing Sheet

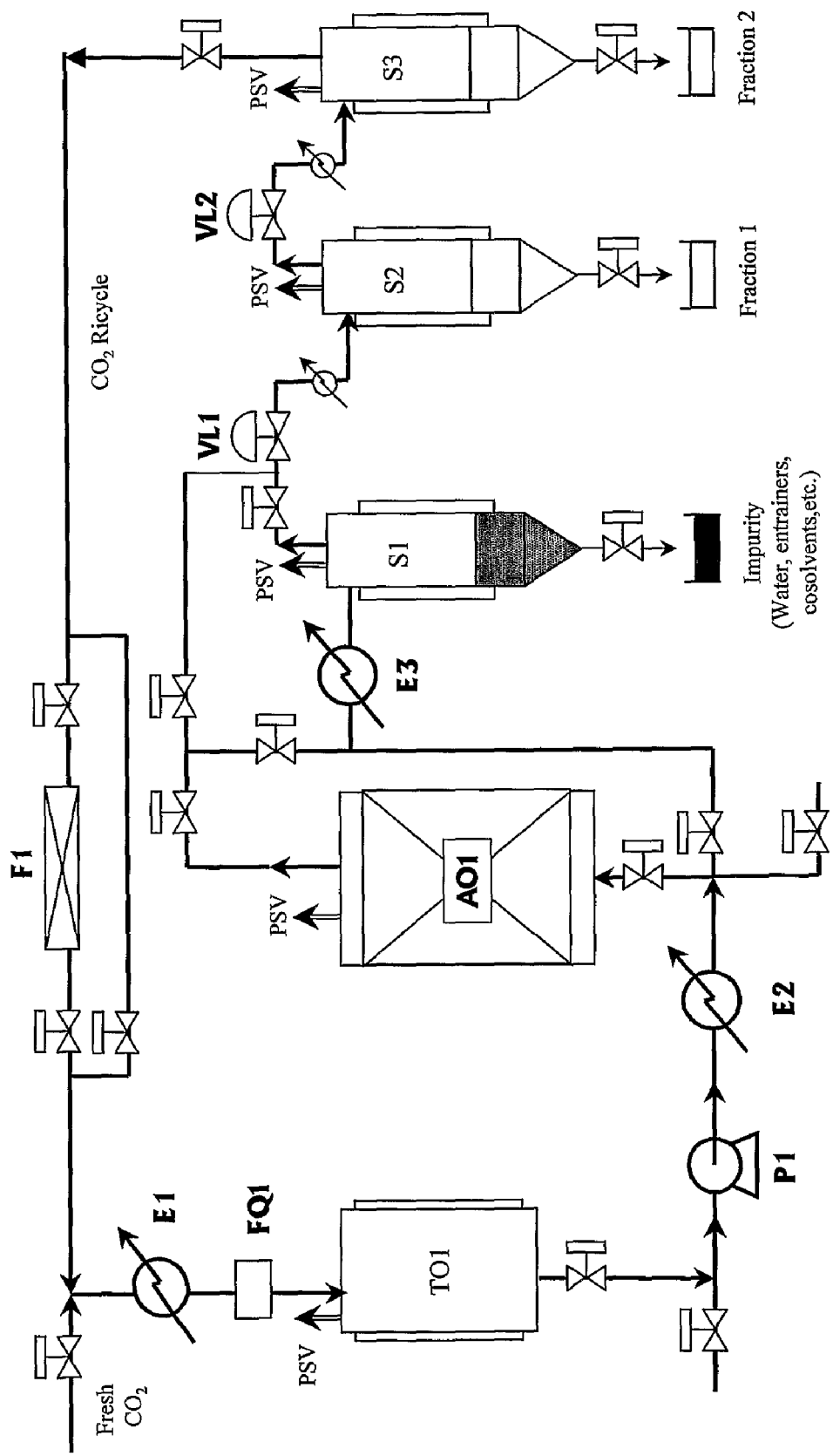

FOOD SUPPLEMENT BASED ON BIOLOGICALLYCOPENE AND PROCESS TO OBTAIN BIOLOGICAL LYCOPENE

BACKGROUND OF THE INVENTION

Technical Field

The present invention relates to a new food supplement, based on biological lycopene.

In the state of the technique, antioxidants, that reduce oxidative damage to cells are quite known. They are both natural or synthetic products. Well-known natural antioxidants are the Ascorbic acid (C-vitamin), Tocopherol (E-vitamin), Retinol (A-vitamin) and Beta-Carotene. One major action of antioxidants is to prevent damage due to the action of Oxygen free radicals, which can damage cells by chemical chain reactions. In addition, antioxidants play an important role in preventing cell aging, arteriosclerosis, cancer and heart diseases. Antioxidant can be found in many vegetables and fruits, among which, tomatoes synthesise a large antioxidant quality. Tomato, in fact, is considered a healthy food due to the fact that it (and its derivatives: peel tomatoes, tomato-sauce, tomato-juice, and similar) are rich sources of carotenoids. Carotenoids are composed of a mixture of Carbon, Hydrogen and sometimes Oxygen. These molecules are built by vegetables, by utilizing simpler molecules; they are responsible for the colours of flowers, fruits, and some roots. For example, carrots gain their orange colour from beta-carotene, the first carotenoid to be isolated at the pure state, which gives the name to the carotenoid family. One of the carotenoids, characterized by high antioxidant property is lycopene, which provide the pigment of the red colour. Fruits and vegetables that are high in lycopene include strawberry, papaya, water-melon, grapefruit and similar. Among which, red tomatoes have the highest concentration of lycopene (from 30 to 400 mg/kg of fresh tomato), which is easily assimilated by the human body in high percentage when fresh, and almost totally upon cooking and/or served in oil-rich dishes for fatty acids generally increases assimilation. Clinical studies have proved that highly beneficial effects of lycopene to prevent some kinds of cancer and other cardiovascular diseases; and to slow down natural cell aging process. Lycopene, in fact, plays an important protective role for his high and specific antioxidant property.

It is also known that lycopene is employed as a basic raw material to prepare food supplements, by means of chemical synthesis (synthetic lycopene) or vegetable bio-synthesis (natural lycopene). In the latter case, the extraction of natural lycopene from vegetables (e.g., tomato) is made by using chemical solvents.

Synthetic lycopene is obtained by means of chemical reactions, known in literature as "Witting process". It is a quite long and complex process, which comprises the production of two intermediates, which react with a third compound yielding raw lycopene, which is, finally, purified by filtration and recrystallization. The end product is a red crystalline solid, characterized by large needle-shaped regular and clean crystals, and a final lycopene concentration of about 95% (impurities and chemical solvents≈5%). Lycopenes are marketed as food colorants (sauces, ketchup, enriched in lycopene) and as an ingredient in food supplement.

The production process of "natural" lycopene starts from fresh tomato (which can be OGM or treated with pesticides and other phytomedicines), which is minced, homogenized and the centrifuged to remove most of the water. The residual humid pasta is the tomato concentrate. Lycopene extraction from the tomato concentrate is made by adding organic solvents with strong agitation. Obviously, together with the lycopene, other lipidic substances and the soluble phytomedicines, are extracted as well. Afterwards, by adding water, the solution is separated in two phases: an organic one, consisting of a solution of organic solvents with lycopene and the other substances extracted, and a liquid phase containing water and the insoluble vegetable residual. By reducing the solubility by solvent evaporation or other, an amorphous precipitate is obtained from the lycopene organic phase; such precipitate (as for the synthetic lycopene) can be purified and recrystallized. The end product has a red-brown colour, partially crystalline, containing chemical solvents and characterized by dirty crystals (impurity inclusions and solvents), more or less large and regular and with a lycopene concentration of about 60%.

The above described lycopene extraction processes present several drawbacks, in terms of efficiency and above all quality of the final product.

Generally, the purity of crystal-shaped end product mainly depends on the purity of the raw materials used and the crystallization and purifying processes adopted. If necessary or convenient, the recrystallization of the end product can be repeated. In the synthesis process, the used raw materials are almost pure; therefore, even with more steps, it is easy to obtain a crystalline solid with 95% purity. On the other side, given the high toxicity of the raw materials (aldehydes and similar) and the solvents used (e.g., toluene) the end product need to be further purified to reduce its toxicity. Moreover, if the synthetic lycopene in crystal is improperly stored (exposed to light or air), it can degrade in mutagenic products; therefore, it is necessary to add antioxidants to prevent or reduce this effect.

In the case of lycopene obtained by the natural process, its toxicity is due both to the chemical solvent residuals in the end product and to the used raw material quality. In fact, tomato berries could have been treated with pesticides and other phytomedicines, would be extracted together with lycopene and be concentrated in the end product. In this process, the lycopene extraction from the tomato berries is made with one or more organic solvents; since in the biological matrix, together with lycopene, there is a large quantity of soluble lipidic substances, which are extracted together with the lycopene. Impurities are natural and not toxic, but, proportionally to their quantity, large quantity of toxic and harmful chemical solvents are also adsorbed. Moreover, oxidation products could be yielded during the process which are very toxic. The natural lycopene, obtained by re-crystallization, could be purified, with an efficiency loss (10-20 in percentage, for each step).

SUMMARY OF THE INVENTION

The present invention aims at creating a new product, to be employed as food supplement, based on "biological" lycopene; and of related natural extraction process of lycopene, which can assure very high purity and quality together with a satisfactory extraction efficiency.

The present invention solves the problems, related to lycopene extraction, being a food supplement, based on biological lycopene, which is extracted from a suitable extraction material (totally or partially vegetable) by means of supercritical carbon dioxide and co-extraction technology. The extraction material to be treated with supercritical carbon dioxide, is made of a mixture, said mixture composed of an extraction matrix and a co-extraction matrix, in the same or different quantities.

Moreover, another object of the invention is the extraction process of lycopene, by means of carbon dioxide in supercritical conditions, from a suitable biological matrix. The carbon dioxide extraction from the above matrix leads to a total extract with a lycopene concentration ranging from 1 to 2%, according to the initial lycopene concentration in the tomato berries. The end product is 100% natural and without any toxic or harmful chemical substance. For this reason, the lycopene is defined as 'biological'. The use of biological lycopene is particularly suitable as high quality food supplement, as well as pharmaceutical and cosmetic product. The quality of lycopene obtained by this process is so different from the one obtained by the traditional processes, that this 'biological' lycopene can be considered as a new product.

These and other advantages will be pointed out in the detailed description of the invention, that will refer to tables 1/4, 2/4, 3/4 and 4/4 in which some experimental results, arising from the process and the product, and an example of the apparatus realizing the co-extraction process are shown. Both are exemplifying and not restrictive.

BRIEF DESCRIPTION OF THE TABLES AND DRAWINGS

With reference to the above mentioned tables:

Table 1 is a summary of the features of the synthetic, natural and biological lycopenes, used to prepare lycopene based food supplements.

Table 2 shows some commercial lycopene-based food supplements (US market, 2005).

Table 3 is a biological lycopene specification.

Table 4 shows the carotenoid characterization.

Table 5 shows the fatty acid characterization.

FIG. 1 is the scheme of the apparatus realizing the extraction with supercritical fluids.

DETAILED DESCRIPTION OF THE INVENTION

Thus, scope of the invention is a total extract from a suitable extraction material, (totally or partially vegetable), by using supercritical carbon dioxide with the co-extraction technology. This extraction material is composed by the mixture of an extraction matrix and a co-extraction matrix, each of them in the same or in different amounts. The extraction matrix is made of tomato berries, which are conveniently processed (washed, purified, concentrated in chromoplasts or other similar processes), dehydrated (cold or warm process, in air or in vacuum, by evaporation, sublimation or other similar process), milled and riddled. The co-extraction matrix can be totally made of each of the following materials or any possible combination between them:

- dry fruit, made of single seeds of peanuts, nuts, almonds, walnuts, pistachios and similar, or any mixing between them;
- oily seeds of sunflower, soy, water melon, citrus fruits, pumpkin, grapefruit, other oily seeds, or any mixing between them;
- leaves and/or branches and/or flowers and/or roots and/or other parts of rosemary, sage, origan, garlic, carrots, cauliflower, other plants, taken alone or in any mixing between them;
- fish meal.

In all cases, the material is conveniently processed, dehydrated and milled.

A further scope of the invention is an optimised process for the lycopene co-extraction from tomato powder, by using supercritical carbon dioxide, consisting in the preparation of the raw materials (first step) and the lycopene extraction and separation from the raw materials (second step), characterised by the contemporary extraction of vegetable oil and other dry fruit compounds and/or oily seeds and/or vegetables and similar. Operative conditions being equal, said vegetable oil as co-solvent improves the lycopene extraction efficiency—up to 10% after 4 h extraction, up to 30% after 8 h extraction, up to 60% for a longer extraction duration—and prevents lycopene degradation. The extraction matrix is a mixture of tomato powder and dry fruit and/or oily seeds and/or other vegetables and/or fish meal. The mixture preparation comprises raw material dehydration (vacuum dehydrated tomatoes, in cold or warm conditions, by evaporation, sublimation or other processes) and the dry tomatoes milling and riddling until a fine powder is obtained; mixing of the obtained tomato powder with the same quantity of dry fruit (almonds, nuts, peanuts and similar) or oily seeds (sunflower seeds, and similar) or vegetables or others and mixture milling. Said mixture is milled until a homogeneous pasta is obtained. The supercritical carbon dioxide pressure ranges between 400 and 600 bar; its temperature ranges between 320 and 373 K. Operative conditions being equal, the carbon dioxide flowrate ranges between 15 and 40 Kg $CO_2$/h; and its density ranges between 0.800 and 0.950 Kg/l. The lycopene extraction phases comprise: $CO_2$ compression and heating, lycopene and other compounds extraction, mixture cooling, first separation phase, pressure reduction, second separation phase and collection of the solute, which precipitates from the mother solution, further pressure reduction, third separation phase with further collection of the solute, $CO_2$ recycling and storage, after filtration and condensation.

The biological process is made with $CO_2$, in a single step and produces a total extract with a lycopene concentration ranging from 1 to 2%. The lycopene concentration in the end oleoresin depends on the matrix properties used for the extraction (lycopene titre, berry quality and maturation degree, pre-treating process). The end product is 100% natural, without any chemical solvent or other toxic and harmful impurities.

The 1-2% lycopene concentration is well suitable for the direct packaging of the product in soft caps or other specialty.

The extraction apparatus with supercritical fluids, schematized in FIG. 1, comprises a 10 l extractor (AO1) and three in-sequence separators (S1, S2), both 1.5 l, and (S3), 0.3 l, respectively. Once the target pressure is reached by the pump (P1), the $CO_2$ flows through a heating coil (E2) before reaching the extraction bed (AO1). Then, leaving (AO1), the flow reaches the separator (S1), through a cooling coil (E3) and, then, the separator (S2), passing through a micrometer valve (VL1), reducing $CO_2$ pressure and density. Precipitating from the mother solution, the solute is collected in (S2). Then, the fluid flow through the separator (S3), and the second micrometer valve (VL2), which reduces its pressure up to the final value; the separated solute is collected in (S3). Exiting the separator (S3), $CO_2$ can be recycled and collected in the tank (TO1), through the filter (F1) and the condenser (E1). The separator (S1) works at a constant pressure; the temperature variation reduces the extract solubility, causing its separation and precipitation. In the separators (S2, S3), the solubility decreases by varying the pressure.

The main difference between synthetic or natural lycopene, extracted by chemical solvents, and the biological lycopene, obtained by supercritical $CO_2$, is that in the first two processes the purification phase is essential, while in the biological process is useless and even damaging. In fact, differently from the other two processes, in the biological process all the substances different from lycopene are natural compounds as well, which are important for individual health and well-being and empower the lycopene anticancer activity. They are phospholipids, Tocopherol (E-vitamin), omega 3 and omega 6 poly-unsaturated fatty acids, other carotenoids (Lutein, Beta Carotene, and similar) extracted from vegetables which play an important role as antioxidants and as lipids, to enhance the lycopene absorption process through the tissues and, consequently, its transfer into the blood (bio-availability). The end product is 100% natural, without any toxicity and suitable to everybody.

The pure or concentrated lycopene is not suitable for direct use by humans, due to several reasons, among which the low bio-availability. However, it is well known that lycopene absorption by the tissues and its transfer into the blood is enhanced by lipidic substances (e.g., vegetable oil). In the preparation of the synthetic lycopene-based commercial product, the lipidic substances must be completely added, to dilute lycopene crystals (almost pure) until the desired final concentration. In the case of the natural lycopene-based commercial product, the lipidic substances must be also added, even if partially already existing in the product itself. On the contrary, in the case of the biological lycopene based commercial product, no addition of exogen lipidic substances is required, since the product contains the necessary lipidic substances. Lycopene structure is another important feature influencing the product bio-availability; in the lycopene case, the structure can be crystalline, amorphous or mixed, with variable crystal percentage. The crystalline structure is more stable than the amorphous one and requires more energy to dissolve into molecules; and, for this reason, it shows less bio-availability than the amorphous structure, which is immediately available. The crystalline or amorphous structures depend on the lycopene production process, the chemical-physical conditions and the management of the solute-solution separation process. In the production process of the synthetic or natural lycopene, its separation from the organic solvent solution can vary in time, but the process always takes two different steps: the nucleation and the crystalline growth. In these processes (synthetic and natural lycopene) the lycopene separation from the mother waters is made to get the purest precipitate: all the substances beside lycopene are toxic impurities and toxic and harmful organic chemical solvents. The end product is totally (synthetic lycopene) or partially crystalline (natural lycopene). Instead, in the biological lycopene production process with supercritical carbon dioxide, the lycopene separation from the solvent solution ($CO_2$) is instantaneous; in fact, the lycopene solubility in the $CO_2$ solution depends on the density (0,8-0,95 kg/l), which depends on the pressure (400-600 bar) and the temperature (320-373 K); in the separator, pressure is rapidly reduced up to 70-150 bar, causing the density reduction up to 0,1 kg/l or less, and this causes the immediate precipitation of the solutes (lipids and lycopene), contained in the solution. Therefore, with this methodology, the standard solute-solution separation process is no more needed, since the lycopene immediately precipitates in a 100% amorphous state.

Table 1 summarizes the lycopene characteristics according to the three production methodologies.

The lycopene-based food supplements are obtained by dilution of the concentrated bulk lycopene (synthetic or natural) with several additives or excipients up to the final concentration value of the active principle (lycopene), which is desired in the formula. Nowadays, the marketed products based on synthetic or natural lycopene, contain a lycopene weight pro dose ranging from 1 mg to 10 mg, corresponding to a lycopene concentration in the end formula ranging from less than 1% up to 10% (weight percentage). Table 2 shows that the US commercial products most required are lycopene food supplements in soft caps, rather than tabs or similar. On the contrary, the biological lycopene-based food supplement represents a new product with respect to the known products on the market: it is exclusively composed of the total extract, which is obtained by treating with supercritical $CO_2$ a suitable biological matrix made of about 50% tomato berries, which are conveniently dehydrated, milled and riddled, and about 50% dry fruits (almonds, walnuts, nuts, peanuts, pistachio and similar) and/or oily seeds, and/or other vegetable or fish meal, conveniently treated and milled. In particular, the extraction matrix is always composed of about 50% tomato powder, while for the other part, it is possible to employ either just one type of dry fruit or oily seeds or other vegetables or fish meal, or one of their possible mixture, so that in the extraction matrix the ratio tomato berries to the other is about 1.

Below some possible combinations are listed.

1) Tomato powder and nuts
2) Tomato powder and almonds
3) Tomato powder and pistachio
4) Tomato powder and walnuts
5) Tomato powder and peanuts
6) Tomato powder and other oily seeds
7) Tomato powder and dry fruit mixture and/or other oily seeds
8) Tomato powder and fish meal
9) Tomato powder and fish meal and dry fruits
10) Tomato powder and vegetable oils and/or fish meal A very important alternative of the extraction matrix is the addition of fish meal to increase the percentage of poly-unsaturated fatty acids in the obtained extract. The lycopene-concentration in the tomato powder can range from 5000 to 15000 mg/kg. The obtained total extract represents the end product, which is directly packaged, without any modification of the composition by adding additives and similar. The lycopene concentration in the total extract ranges from 1% to 2%, depending on the lycopene concentration in the treated tomato berries. The carotenoids come entirely from the tomato, while the lipidic portion, the tocopherols (E vitamin), the poly-unsaturated fatty acids and other compounds come from both the tomato and the co-matrix.

Since the lycopene concentration in the final extract depends on the lycopene concentration in the fresh tomato berries, in the extraction product the lycopene concentration is absolutely natural, as for the food supplements, synthetic or natural lycopene based, where the lycopene concentration in the end formula can be easily varied, depending on the amount of additive (e.g., due to commercial needs).

A further characteristic of the biological lycopene, with respect to the natural one, is the small time interval between the CO2 treatment of the matrix and the end product packaging.

The bulk biological lycopene specification, which is also the specification of the final food supplement, is reported in Table 3. The quantity and the kind of carotenoids in the extract depend on the variety of the tomato berry, its maturation degree, the climatic and cultivation conditions and the pre-treatment. In Table 4 the share of the normally available carotenoids is shown. The quantity and the kind of the lipidic substances in the extract depend on both tomato berries characteristics and the used co-matrix. In the case of a nuts co-matrix, the fatty acids composition is reported in Table 5. The CO2 extracted oleoresin, together with the carotenoids family, which is available in the fresh berry, also contains remarkable quantities of essential poly-unsaturated fatty acids (PUFA). They are: linoleic acid (omega-6) and alfa-linolenic acid (omega-3).

TABLE 1

| Product | Synthetic Lycopene | Natural Lycopene | Biological Lycopene |
|---|---|---|---|
| Raw material | Synthetic raw materials | Tomato berries (no regulation). Use of OGM, pesticides, phytomedicines, etc., is possible | Certified biological tomato berries. No OGM, pesticides, phytomedicines, etc. |
| Production technology | Chemical synthesis reactions between synthetic compounds | Tomato extraction with chemical solvents (THF, etc.) | Biological tomato extraction with supercritical CO2 |
| Bulk end product | Crystalline. Clean, regular and big crystals. Lycopene: 90-95%. Impurities and chemical solvents | Amorphous and crystalline. Irregular and dirty crystals. Lycopene: 50-60%. Impurities and chemical solvents | Amorphous. Lycopene suspension (1-2%) in tomato Natural Lipids |
| Bulk end product purification | Mandatory. All different from lycopene are impurities and toxic-harmful chemical solvents | Mandatory. All different from lycopene are impurities and toxic-harmful chemical solvents | Not needed. 100% natural product |
| Commercial formula | 1-10% Dilution, with lipids + other exogen chemical additives | 1-10% Dilution, with lipids + other exogen chemical additives | As extracted |
| Toxicity | Possible presence of impurities and toxic/harmful solvents | Possible presence of impurities and toxic/harmful solvents (pesticides ?) | Absent |
| Bio-availabilty | Improved by exogen lipids and other chemical additives | Improved by exogen lipids and other chemical additives | Optimal. Presence of Lutein, poly-unsaturated fat acids, E-vitamin, etc. |
| Natural | Zero. Completely synthetic product with possible impurities and chemical solvents | Low. Natural product with chemical solvents and exogen chemical additives | Maximum. Only what is present in the tomatoes is extracted, boxing up as it is |

TABLE 2

| Specialty | Packaging (%) |
|---|---|
| Soft caps | 64% |
| Caps | 17% |
| Tabs | 14% |
| Liquid | 2% |
| Other | 2% |

TABLE 3

| Raw material | Tomato berries, produced according to biologic regulation; non OGM berries; no pesticides and other phytomedicines and the like. |
|---|---|
| Co-extraction matrix | Nuts, almonds and the like/oily seeds, vegetables, other. |
| Production technology | Supercritical carbon dioxide extraction, by co-extraction technology |
| Bulk product | Fluid-oily suspension of Lycopene in natural vegetable lipids, having characteristic smell. |
| Colour | Dark red/brown |
| Viscosity | (Broockfield, R3, 20 rpm, 25° C.) 1500-3000 cPs |
| Specific weight (20°): | 0.928-0.948 kg/l |
| Composition | |
| Lycopene | 1-2% (HPLC Titre) |
| Other Carotenoids | <2% (Lutein, Beta Carotene, Zeaxanthin, and the like) |
| Others constituents: | Difference to 100%. Natural compounds, coming from the vegetable matrix and co-extracted with the Lycopene, as: phospholipids, poly-unsaturated fatty acids, tri-glycerides, di-glycerides, sterols, sterol esthers, sugars, other anti-oxidant and the like |
| E-vitamin (alfa-tocopherol, and the like): | 0.2-0.5% |
| Other (tomato powder) | 1-3% |

TABLE 4

| Carotenoids | Carotenoids percentage |
|---|---|
| Total Lycopene (cis + trans) | 82-88% |
| Total Beta-Carotene (cis + trans) | 3-6% |
| Lutein (cis + trans) | 2-3% |
| Other Carotenoids | 5-10% |

TABLE 5

| Fatty acids | Fatty acids percentage |
|---|---|
| Oleic acid (C18:1) | ≈80% |
| Linoleic acid (C18:2) | ≈9% |
| Linoleic acid (C18:3) | ≈1% |
| Palmitic acid (C16:0) | ≈5% |
| Stearic acid (C18:0) | ≈2% |
| Others | ≈3% |

What I claim is:

1. A process for the co-extraction of organic lycopene from tomato berries completely free of pesticides, phytomedicines and other toxic substances; said process is carried out without the use of harmful and chemical solvents, using supercritical carbon dioxide, consisting of the following phases:
   a) Vacuum dehydrating riddled tomato berries, by applying cold or warm conditions, evaporating and sublimating;
   b) Riddling and milling of the dry tomato berries until a fine powder is obtained;
   c) Mixing the obtained tomato powder with the same quantity of a mixture of nut components selected from the group consisting of almonds, peanuts, walnuts, pistachios;
   d) Adding oily seeds, such as seeds selected from the group consisting of sunflower, soy, water melon, citrus fruits, pumpkin, grapefruit, and adding other vegetables selected from the group consisting of rosemary, sage, oregano, garlic, carrots, cauliflowers, and adding fish meal;
   e) Milling and dehydrating said mixture until a homogeneous paste is obtained;
   f) Applying supercritical $CO_2$, at a specific density, flow rate, pressure and temperature;

g) Extracting lycopene simultaneously to the extraction of other compounds, such as natural lipids, Lutein, Beta-Carotene, Zeaxanthin, E-vitamin wherein said extracted lycopene has a 100% amorphous structure;
h) Mixture cooling;
i) Pressure reducing;
j) Collecting the solution, which precipitates from the mother solution;
k) Further pressure reducing;
l) Filtrating, condensing and collecting the solution in a storage tank, including the $CO_2$ recycling.

2. A process according to claim 1, wherein said supercritical carbon dioxide pressure ranges between 400 and 600 bar.

3. A process according to claim 1, wherein the supercritical carbon dioxide temperature ranges between 320 and 373 degrees Kelvin.

4. A process according to claim 1, wherein said supercritical carbon dioxide flow rate varies between 15 and 40 Kg $CO_2$/h.

5. A process according to claim 1, wherein said supercritical carbon dioxide density ranges between 0.8 and 0.95 kg/l.

* * * * *